United States Patent
Iwabuchi et al.

(10) Patent No.: US 7,087,016 B2
(45) Date of Patent: *Aug. 8, 2006

(54) HEALTH MANAGEMENT DEVICE AND HEALTH MANAGEMENT SYSTEM

(75) Inventors: Tamotsu Iwabuchi, Tokyo (JP); Miyuki Kodama, Tokyo (JP); Ikuo Hakomori, Tokyo (JP)

(73) Assignee: Tanita Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/984,153

(22) Filed: Oct. 29, 2001

(65) Prior Publication Data

US 2002/0026113 A1 Feb. 28, 2002

Related U.S. Application Data

(63) Continuation of application No. 09/500,480, filed on Feb. 9, 2000, now Pat. No. 6,327,495.

(30) Foreign Application Priority Data

Feb. 9, 1999 (JP) ................................. 11-31229

(51) Int. Cl.
    *A61B 5/00* (2006.01)
(52) U.S. Cl. ....................................... 600/300; 600/547
(58) Field of Classification Search ........ 600/300–301, 600/547
    See application file for complete search history.

(56) References Cited

U.S. PATENT DOCUMENTS

| 4,895,163 | A | | 1/1990 | Libke et al. | |
|---|---|---|---|---|---|
| 4,947,862 | A | | 8/1990 | Kelly | |
| 4,949,727 | A | | 8/1990 | Yamazaki et al. | |
| 5,372,141 | A | * | 12/1994 | Gallup et al. | 600/547 |
| 5,579,782 | A | | 12/1996 | Masuo | |
| 5,697,376 | A | * | 12/1997 | Nomura et al. | 600/300 |
| 5,817,031 | A | * | 10/1998 | Masuo et al. | 600/547 |
| 5,827,180 | A | * | 10/1998 | Goodman | 600/300 |
| 6,088,615 | A | | 7/2000 | Masuo | |
| 6,095,949 | A | | 8/2000 | Arai | |
| 6,122,351 | A | * | 9/2000 | Schlueter, Jr. et al. | 600/301 |
| 6,159,147 | A | * | 12/2000 | Lichter et al. | 600/300 |
| 6,243,561 | B1 | * | 6/2001 | Butler et al. | 600/547 |
| 6,295,506 | B1 | * | 9/2001 | Heinonen et al. | 600/300 |
| 6,354,996 | B1 | * | 3/2002 | Drinan et al. | 600/300 |

(Continued)

FOREIGN PATENT DOCUMENTS

EP 0 926 488 A2 6/1999

(Continued)

*Primary Examiner*—Robert L. Nasser
(74) *Attorney, Agent, or Firm*—McDermott Will & Emery LLP

(57) ABSTRACT

A health management device comprises at least four electrodes provided on a main body of an intelligent terminal unit; a constant current generating unit which applies a constant current to at least two electrodes among said at least four electrodes; a voltage detecting unit which detects a voltage of at least two electrodes among said at least four electrodes; a numeral input unit provided on said intelligent terminal unit; a display unit provided on said intelligent terminal unit; a switching unit which switches a function as an intelligent terminal unit into a function as a health management device and vice versa; and a control unit which calculates a health management indicator based on data input from said numeral input unit and a detected data from said voltage detecting unit and displays a calculated result on said display unit when said function being switched into the function as the health management device by said switching unit.

22 Claims, 5 Drawing Sheets

U.S. PATENT DOCUMENTS

| | | | |
|---|---|---|---|
| 6,368,273 B1 * | 4/2002 | Brown | 600/300 |
| 6,379,301 B1 * | 4/2002 | Worthington et al. | 600/300 |
| 6,468,209 B1 * | 10/2002 | Heymsfield et al. | 600/300 |
| 6,602,191 B1 * | 8/2003 | Quy | 600/300 |

FOREIGN PATENT DOCUMENTS

| | | |
|---|---|---|
| WO | WO 97/49077 | 12/1997 |
| WO | WO 98/55015 | 12/1998 |

* cited by examiner

HEALTH MANAGEMENT DEVICE AND HEALTH MANAGEMENT SYSTEM

CONTINUING DATA

This application is a continuation of U.S. Ser. No. 09/500,480, filed Feb. 9, 2000, now U.S. Pat. 6,327,495.

BACKGROUND OF THE INVENTION

1. Field of the Invention

The present invention generally relates to a health management device, and, more particularly, to a body fat meter which is mounted on an intelligent terminal unit such as a portable telephone, a portable personal computer with a modem or an electronic organizer with communication system and shares a numeral input means and a display means therewith, which are inherently provided for said intelligent terminal unit. The present invention also relates to a health management system in which a body fat meter, a blood pressure manometer, a pulse monitor, etc. is mounted on a intelligent terminal unit such as a portable telephone or the like and shares the numeral input means and the display means therewith, which are inherently provided for said intelligent terminal unit, and transmits/receives various data concerning the body fat, the blood pressure, the pulse rate, etc. to/from an aggregation center.

2. Description of the Prior Art

Recently, the body fat meter has been spread over many families based on a concept that one shall control one's health by oneself. There has been proposed several types of body fat meters including an integral type body fat meter incorporated into a weight measuring scale, a grip type body fat meter gripped by both hands in use for measuring, and furthermore a card type body fat meter capable of being carried with. However, since these body fat meters are, with an exception of the integral type one incorporated into a weight measuring scale, exclusive machines for measuring a body fat percentage and are not used for any other uses, there is a problem that a certain place has to be prepared for keeping it. In addition, some of these body fat meters are too large to be carried with while going outdoor therewith, or, in case of the card type one, it is too small so that sometimes it is forgot to be carried with. Further, the integral type one incorporated into the weight measuring scale is generally used in a bathroom or the like in a home and is not suitable for being taken out of the house and being used in the outdoors.

Said body fat meter is constructed as an independent unit from a mechanical and electrical viewpoint, so that, when a measured data is analyzed by a special facility in various ways, the measured data shall be delivered by, for example, a mail or the body fat meter itself including a measured data stored therein shall be brought into the special facilities.

Portable blood pressure manometers and pulse monitors have also been developed and used. However, in these prior devices, the measured data have been delivered to a special facility by a mail, or the device itself including a measured data stored therein has been brought into the special facility, to analyze the data, as in a body fat meter mentioned above.

The present invention is achieved in the light of the problems described above, and the object of the invention is to provide a health management device which is mounted on an intelligent terminal unit such as portable telephone, which is usually carried with, and causes no problem for keeping it in a certain place, and allows a body fat percentage to be measured at any time at any place.

Another object of the present invention is to provide a health management system which allows various data concerning a measurement of the body fat percentage to be analyzed from a specialized viewpoint based on a communication with a large-scale aggregation center by the use of communication function installed in the intelligent terminal unit with body fat meter, and also allows various data to be fed back to the user of the intelligent terminal unit by sending back an analyzed data using said communication function.

Another object of the present invention is to provide a health management system which allows various data concerning the blood pressure, the pulse rate, etc. of a patient or a user to be fed back to the patient or user.

SUMMARY OF THE INVENTION

According to an aspect of the present invention, there is provided a health management device comprising:

at least four electrodes provided on a main body of an intelligent terminal unit;

a constant current generating unit which applies a constant current to at least two electrodes among said at least four electrodes;

a voltage detecting unit which detects a voltage of at least two electrodes among said at least four electrodes;

a numeral input unit provided on said intelligent terminal unit;

a display unit provided on said intelligent terminal unit;

a switching unit which switches a function as an intelligent terminal unit into a function as a health management device and vice versa; and a control unit which calculates a health management indicator based on data input from said numeral input unit and a detected data from said voltage detecting unit and displays a calculated result on said display unit when said function being switched into the function as the health management device by said switching unit.

According to another aspect of the present invention, there is provided a health manaegement system characterized by that:

an intelligent terminal unit having a numeral input unit, a display, unit, a transmitting and receiving function unit, a memory unit or the like comprises:

at least four electrodes;

a constant current generating unit which applies a constant current to at least two electrodes among said at least four electrodes;

a voltage detecting unit which detects a voltage of at least two electrodes among said at least four electrodes;

a switching unit which switches a function as an intelligent terminal unit into a function as a health management device and vice versa; and a control unit which calculates a health management indicator based on data input from said numeral input unit and a detected data from said voltage detecting unit and displays a calculated result on said display unit when said function being switched into the function as the health management device by said switching unit;

an aggregation center which performs analysis based on a data from said intelligent terminal unit and transmits a result data of said analysis to said intelligent terminal unit is provided; and a data communication is performed between said intelligent terminal unit and said aggregation center.

According to still another aspect of the present invention, there is provided a health management system comprising:

a connector section provided on a main body of an intelligent terminal unit which connects probe unit which can be attached to predetermined portions of the body of a patient to detect predetermined biological parameters of the patient;

activating unit which activates said probe unit connected to said connector section to cause said probe unit to detect said predetermined biological parameters of the patient;

a numeral input unit provided on said intelligent terminal unit;

a display unit provided on said intelligent terminal unit;

a switching unit which switches a function as an intelligent terminal unit into a health management function and vice versa; and a control unit which calculates a desired health management parameter of the patient on the basis of data input from said numeral input unit if it is required for calculating said desired health management parameter of the patient and said predetermined biological parameters detected by said probe unit and displays a calculated result on said display unit when said function being switched into said health management function by said switching unit.

According to still another aspect of the present invention, there is provided a health management system characterized by that:

an intelligent terminal unit having a numeral input unit, a display unit, a transmitting and receiving function unit, a memory unit or the like comprises:

a connector section which connects probe unit which can be attached to predetermined portions of the body of a patient to detect predetermined biological parameters of the patient;

activating unit which activates said probe unit connected to said connector section to cause said probe unit to detect said predetermined biological parameters of the patient;

a switching unit which switches a function as an intelligent terminal unit into a health management function and vice versa; and a control unit which calculates a desired health management parameter of the patient on the basis of data input from said numeral input unit if it is required for calculating said desired health management parameter of the patient and said predetermined biological parameters detected by said probe unit and displays a calculated result on said display unit when said function being switched into said health management function by said switching unit;

an aggregation center which performs analysis based on a data from said intelligent terminal unit and transmits a result data of said analysis to said intelligent terminal unit is provided; and a data communication is performed between said intelligent terminal unit and said aggregation center.

In order to measure a body fat percentage between both hands, said four electrodes are provided so that two fingers per a hand may be brought into contact with the electrodes.

Besides, in order to measure the body fat percentage between both feet or between hand and foot adding to between both hands, preferably, four more electrodes are added further so that both feet may be brought into contact with the electrodes.

It is advantageous that said intelligent terminal unit stores the data of the body fat percentage calculated by said control unit in the memory unit for storing telephone numbers or the like in order to make it possible to check a past data of the body fat percentage and a variation history thereof.

Further, it is preferable that the body fat percentage is measured and calculated at a time set in an alarm function by the use of the alarm function of said intelligent terminal unit.

Said data transmitted from the intelligent terminal unit may be a data of the body fat percentage calculated by said control unit.

Said data transmitted from the intelligent terminal unit may be a data of the body fat percentage stored in said memory unit.

It is preferable that said display unit displays various data transmitted from said aggregation center by the use of a receiver function of said intelligent terminal unit.

It is preferable that said memory means stores various data transmitted from said aggregation center by the use of a receiver function of said intelligent terminal unit.

The data used in said data communication may be a data indicating a desirable range of the body fat percentage.

The data transmitted from said aggregation center may be a data of an amount of fat to be reduced.

The data transmitted from said aggregation center may be a data of quantity of exercise to be taken.

The data transmitted from said aggregation center may be a data of an amount of meal to be reduced.

Furthermore, said health management parameter may be a blood pressure.

Furthermore, said health management parameter may be a pulse rate.

There will now be described an embodiment of the invention with reference to the attached drawings.

DESCRIPTION OF THE PREFERRED EMBODIMENTS

A: Constitution of the Embodiment

Figure 1:
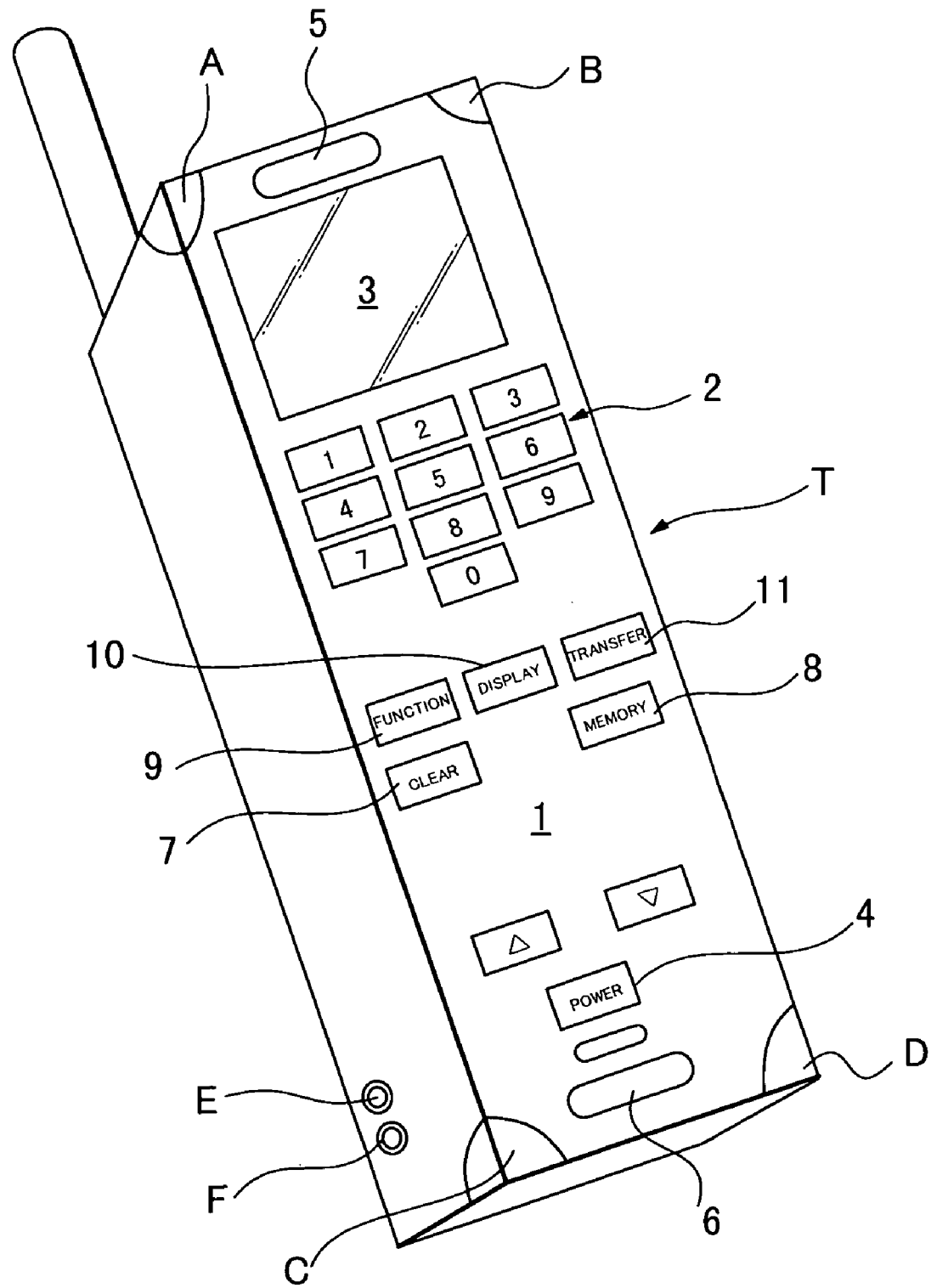
FIG. 1 is a schematic perspective view of the portable, telephone set with body fat meter according to an embodiment of the present invention.
Figure 3:
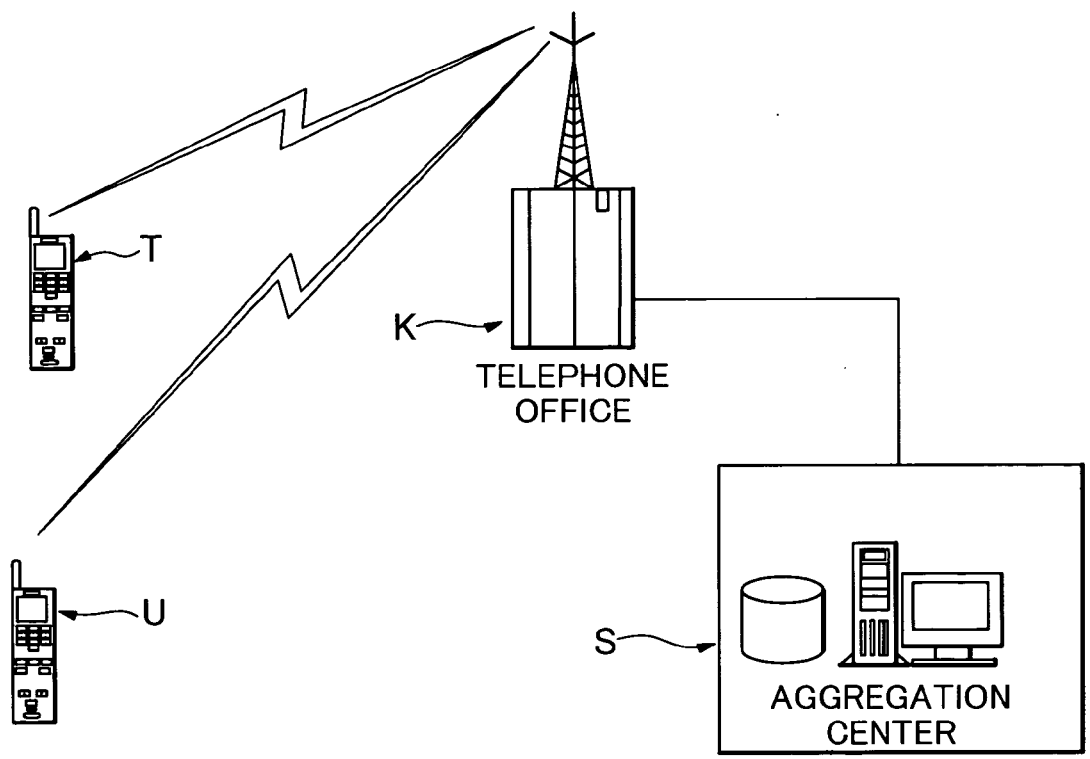
FIG. 3 is a diagram illustrating a health management system using the portable telephone set with body fat meter of FIG. 1.

An embodiment of FIG. 1 shows a case where a portable telephone set "T" is used as an intelligent terminal unit, in which said portable telephone set "T" is configured, as shown in FIG. 3, so as to transmit a data via a telephone office "K" to an aggregation center "S" having a special information about health management data analysis and lots of advisory information and also so as to receive a data from the aggregation center "S". This portable telephone set "T" is configured so as to be capable of transmitting/receiving a data to/from a portable telephone set "U" of other person same as a normal telephone set is.

The portable telephone set "T" is provided, on an front surface of a main body 1 made of insulating plastic or the like, with a numeral input unit 2 composed of ten-key pad for inputting a number of a telephone to be called, a display unit 3 composed of LCD or the like for indicating a number input from said numeral input unit 2 and a communication condition as a portable telephone, a power source switch 4, a speaker 5, a microphone 6, a clear-key 7 for erasing a data input from said numeral input unit 2, and a memory key 8 for storing a number input from said numeral input unit 2. In addition, though not described in details herein, this portable telephone set is provided with another function in which a plurality of stored telephone numbers is displayed and a desired one is selected to be called, and also is provided with an indicator means including a buzzer for incoming calls, which are functions as a normal telephone set.

The portable telephone set "T" is provided with electrically conductive electrodes "A", "B", "C" and "D" at four corners of the front surface of the main body 1 thereof respectively so that two fingers of the right hand and two fingers of the left hand may be brought into contact with respective electrodes. On the front surface of the main body 1, there are provided a change-over switch 9 for selecting a function among those including a function for using as a normal telephone, a function for inputting a personal data such as sex, height, weight or age used when the body fat percentage being measured, and a function for storing the data of the body fat percentage, a display change-over switch 10 for changing a display of a data concerning body fat to that of BMI and the body fat percentage, and a transfer switch 11 for transmitting a data of the body fat percentage, which is measured or stored, to the aggregation center and for displaying a data received from the aggregation center or storing it in the memory.

Further, connectors "E" and "F" for connecting four electrodes which are brought into contact with soles of both feet are mounted on a side surface of said main body 1. Each of said connectors "E" and "F" is configured so that an exterior type electrode body having two electrodes to be brought into contact with each of the right or the left foot (which is used in a separate electrode type body fat meter, though not shown) may be connected. The body fat measurement using four or eight electrodes will be omitted since it has been well known.

Figure 2:
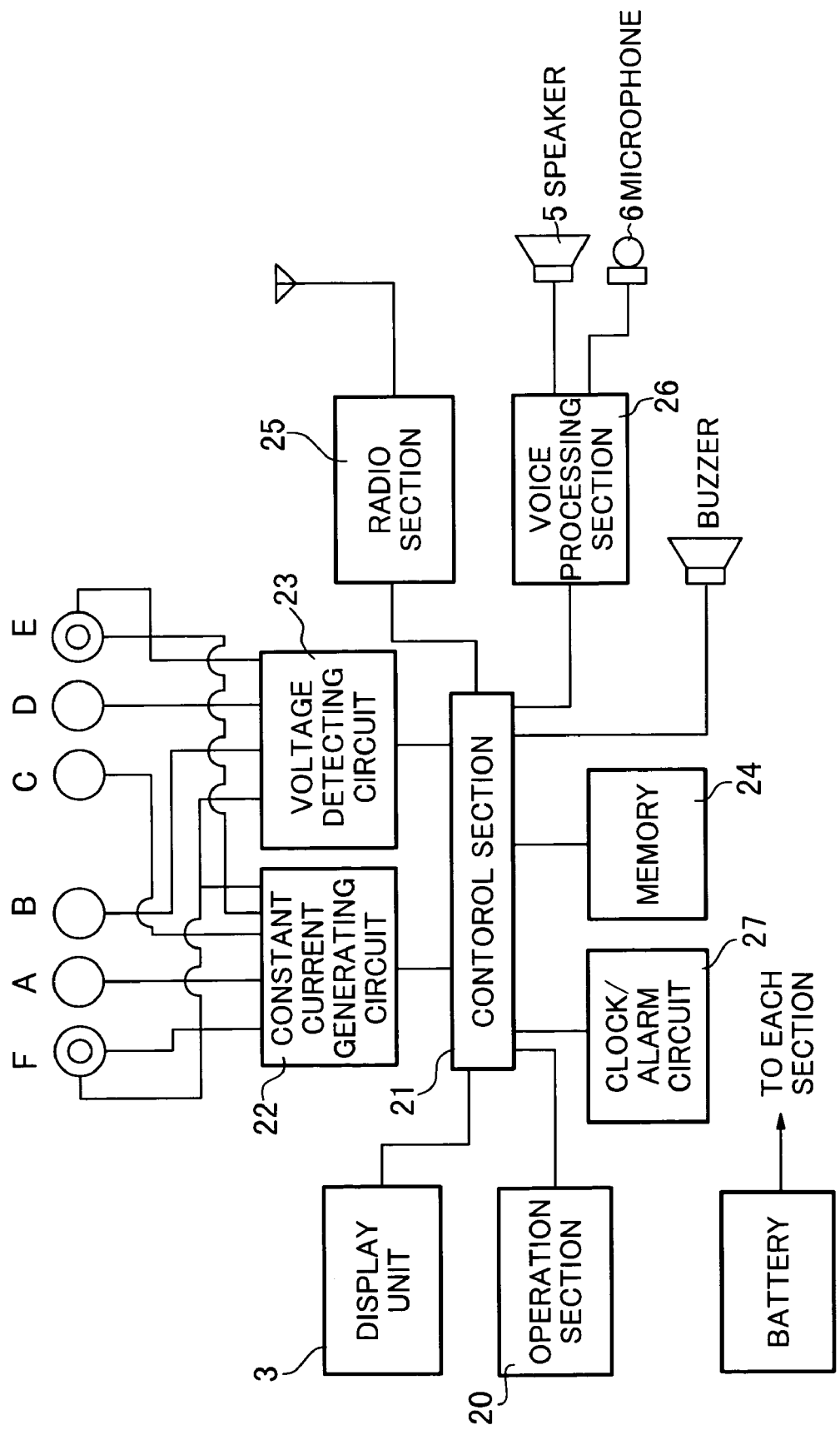
FIG. 2 is a block diagram illustrating an electric configuration of the portable telephone set with body fat meter of FIG. 1.

FIG. 2 is a block diagram illustrating an electric configuration of the portable telephone set of FIG. 1 and a detailed description of the well known configuration of the portable telephone set will be omitted. An operation section 20 includes the function change-over switch 9, the display change-over switch 10, the transfer switch 11 adding to the numeral input unit 2, the clear key 7, the memory key 8 or the like which are provided on the normal portable telephone set. A constant current generating circuit 22 selectively, applying a-constant current to each of the right and the left hands and feet, and a voltage detecting circuit 23 for detecting a voltage applied to hands or feet by said constant current generating circuit 22 are connected to a control section 21 including a microcomputer which controls overall system. A memory 24 stores telephone numbers to be called as a normal portable telephone set as well as the data concerning the body fat measurement and the received data from the aggregation center "S". A radio section 25 and a voice processing section 26 are the same as those of the normal portable telephone set.

The control section 21 includes also a well known speech synthesis circuit which enables the received data from the aggregation center "S" or the data stored in the memory 24 to be output in voice by the speaker 5 through the voice processing section 26. Further, a well known clock/alarm circuit 27 which is provided with a clock function for displaying a current time on the display unit 3 and an alarm function for generating an alarm sound through the buzzer or the speaker 5 at a predetermined time is connected to the control section 21.

B: Operation of the Embodiment

Figure 4:
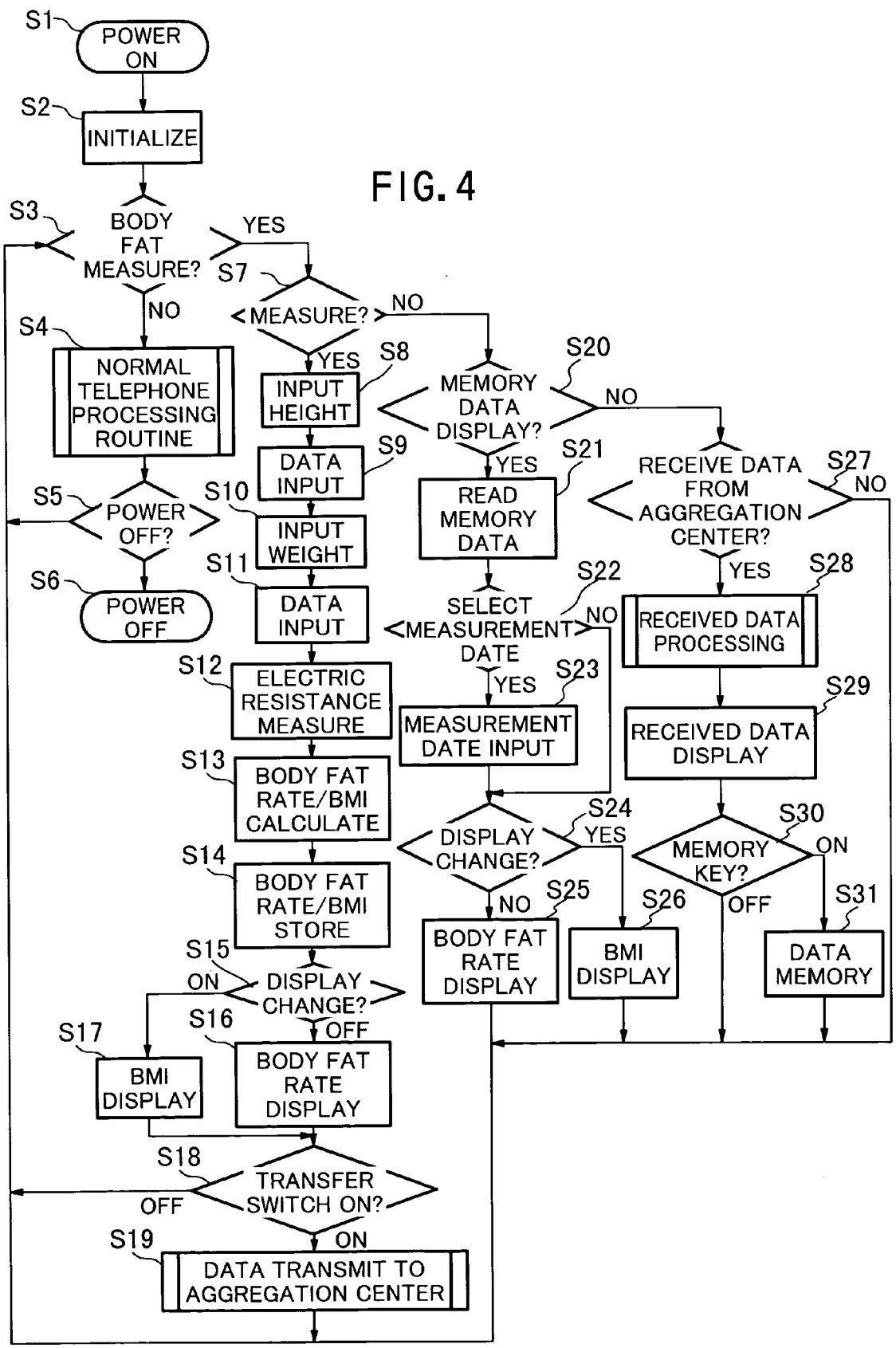
FIG. 4 is a schematic flow chart of the portable telephone set with body fat meter of FIG. 1.

At first, the case where the body fat is measured by the portable telephone set "T" will be described with reference to the schematic flow chart of FIG. 4. This flow chart shows an outline of a concept of various processings and may differ from actual flow chart in some points. At first, the power source switch 4 is turned on and then the process moves from step 1 to step 2 to initialize an operation of the portable telephone "T". At that time, since the normal telephone function is set, the process determines to be "no" at step 3 and moves to step 4. Since the process in step 4 is conventional one and is well known, the description thereof will be omitted. Then, the state of the power source is determined at step 5 and the processes between steps 3 and 5 are repeated until the power source is turned off by the power source switch 4. When the power source switch 4 is turned off, the power source of the whole system of the portable telephone "T" is turned off at step 6.

When the function change-over switch 9 is pushed while the power source of the portable telephone set "T" is in "on" state, the process determines to be "yes" at step 3 to moves to the body fat measurement mode in step 7. At step 7, since the process is in the state for measuring the body fat because the function change-over switch 9 is pushed once, the process determines to be "yes" and moves to step 8 where the control section 21 sends to the display unit 3 a signal for demanding the height data to be input and thereby the display unit 3 displays a character message for demanding the height data to be input. When this message is displayed and an operator inputs his own height data by the numeral input unit 2 and turns on the memory key 8 (step 9), the process moves to step 10 where the display unit 3 displays a character message for demanding the weight data to be input. At step 11, when the operator inputs his own weight data by the same operation as of the height data at step 9, the process moves to the step 12 where the display unit 3 displays a character message for measuring the body fat percentage. This message requests the operator to bring his forefinger and thumb of his right hand into contact with the electrodes "A" and "B" and to bring his forefinger and thumb of his left hand into contact with the electrodes "C" and "D", and notifies him that the body fat percentage will be measured. When this notification message is displayed, the constant current circuit 22 applies the current between the forefingers of the right and the left hands through the electrodes "A" and "C". Then the voltage detecting circuit 23 detects the voltage between the thumbs of the right and the left hands through the electrodes "B" and "D".

This detected data is sent to the control section 21 where an electric resistance between the thumbs of the right and the left hands of the operator is calculated based on the formula below:

$$\text{detected voltage value/constant current value} = \text{resistance value}$$

At step 13, a body mass index (BMI) is calculated based on the height and the weight data, and the body fat percentage is calculated based on a well known equation using data such as the height or the like having been input and the electric resistance value measured, and, at step 14, above calculated values as well as data including a measurement date, the height, the weight, the sex, the age, and the electric resistance value are stored in the memory 24. At step 15, the condition whether the display change-over switch 10 on the front surface of the portable telephone set is turned-on or not is determined, and, if it is not turned-on, the process moves to step 16 and displays the calculated body fat percentage on the display unit 3. When the display change-over switch 10 has been turned on, the process moves to step 17 and displays the calculated BMI on the display unit 3. Thus, the body fat percentage and the BMI which are data for health management can be easily displayed alternatively by the use of the display change-over switch 10.

Though only the calculated body fat percentage and BMI are displayed at steps 16 and 17 in the above description, all or a part of the other data stored at step 14 can be selectively displayed at the same time. At step 18, the condition whether the transfer switch 11 on the front surface of the portable telephone set is turned on or not is determined, and, if it is in "off" condition, the process returns to step 3, and, if it is in "on" condition, the process moves to step 19, where the process makes a telephone call to the aggregation center "S" and transmits various data stored at step 14 along with the telephone number of the transmitter and, after the transmission, cuts off the call and returns to step 3. The reason why the telephone number of the transmitter is transmitted is that a well known function of transmitter number notification is used, which allows the aggregation center "S" receiving the transmitted data to easily call the data such as name of the transmitter by the computer based on the telephone number, to store these data in the predetermined area of database, and to easily analyze the data. This analysis or the like will be described later.

Then, in the body fat measurement mode at step 7, when the function change-over switch 9 is turned on again, the process moves from step 7 to steps 20, 21 to enter a memory data display mode. At step 21, various past data stored in the memory 24 are called to the control section 21 and the stored data of the measurement date is displayed as a list on the display unit 3 (step 22). The transmitter selects a specified measurement day on the list by the input unit 2 (step 23). After the selection, the body fat percentage and BMI are displayed as in the processing at steps 15 to 17 (steps 24 to 26), and the process returns to step 3. Thereby, the transmitter can look at the past measured data of the body fat percentage and a history of the data. In addition, when the function change-over switch 9 is turned on in the memory data display mode at step 20, the process moves from step 20 to step 27, where the process makes a telephone call to the aggregation center "S" by the use of the normal telephone function and receives the data analyzed in the aggregation center "S". At that time, the aggregation center "S" determines the telephone number based on the telephone call and transmits the necessary data from the database of the objective person.

At step 28, the portable telephone "T" processes the received data and displays it as a character information on the display unit 3 at step 29. This displayed character information can be stored in the memory 24 by turning on the memory key 8 at step 30. Though this stored data is not described in the flow chart, it can be displayed on the display unit 3 by turning on the memory key 8 and selecting it. Thereby, an ordinary transmitter can receive various advice based on the specialized analysis by the aggregation center to utilize it in judging own health condition and in managing own health based on the quantity of exercise to be taken, the restriction on the amount of meal or the like.

When the aggregation center "S" makes a telephone call to the portable telephone "T" to send the data, the portable telephone "T" can implement the processes between steps 26 to 29 by turning on the transfer key 11 after the data is received.

Further, the clock/alarm circuit 27 of FIG. 2 can sound the buzzer at the predetermined time in a day to notify that the daily time for measuring the body fat has come, and, if the alarm time is linked to the body fat measuring function, a character display for indicating the body fat measuring time may be shown on the display unit 3 at the same time when the buzzer is sounded at the predetermined time. This enables an accurate and continuous measurement of the body fat, which has to be implemented everyday at the predetermined time, by preventing the measurement from being forgotten or from being implemented at a time other than the predetermined one.

In addition, contents of the character display on the display unit 3 may be output in voice by the speech synthesis circuit in the control section 21 through the voice processing section 26 and the speaker 5.

The portable telephone set "T" can transmit or receive the various data described above to or from another portable telephone set "U" of the other person by the same manner employed when said portable telephone set "T" communicates with the aggregation center "S" in transmitting or receiving various data.

Then the data analysis processing in the aggregation center "S" will be described.

The aggregation center stores various data such as measurement date, height, weight, sex, age, electric resistance value, BMI, body fat percentage for each transmitter from the portable telephone set in a form of database, and also stores the contents of various advice for each transmitter based on the analysis of these data and the time when the contents of advice is delivered to the transmitter. Upon receiving a telephone call from the portable telephone of the transmitter, the aggregation center at first confirms the telephone number of the transmitter and determines who is sending the data. After the determination, the aggregation center "S" stores the data sent from the portable telephone in said database and also stores the contents of various advice based on the analysis of the data.

Said stored contents of various advice may be sent back immediately after the data sent from the portable telephone was received or may be transmitted when the transmitter requires as shown at and after step 27 of FIG. 3. In addition, the aggregation center "S" may transmit periodically or at any time, voluntarily or urgently.

Figure 5:
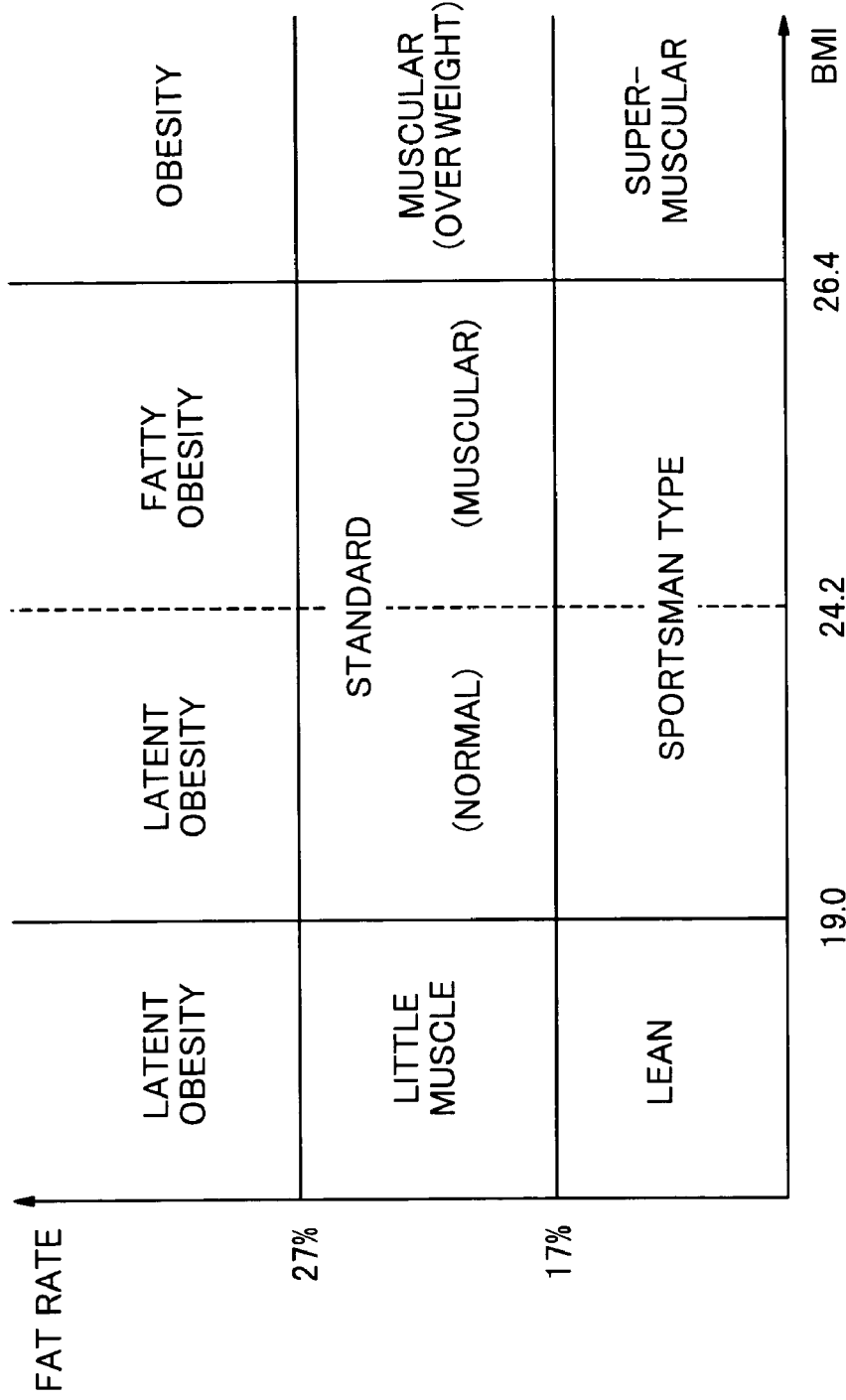
FIG. 5 is a chart illustrating a balance between BMI and the body fat percentage.

Said contents of various advice includes a data indicating if the body fat percentage being within a desirable range, a data indicating how much Kg of fat shall be reduced to go into the desirable range, or the like. If the display means 3 of the portable telephone set "T" is capable of making a bit map display, a balance between the BMI and the body fat percentage may be displayed as a matrix as shown in FIG. 5 to notify the transmitter if the current body fat percentage is within the desirable range or which position it belongs to. The amount of fat (Kg) to be reduced described above may be calculated by the equation below:

Amount of fat to be reduced=Current weight×(Current body fat percentage−Desired body fat percentage)/(100−Desired 10 body fat percentage)

When the amount of fat to be reduced is made clear, an additional advice concerning the quantity of exercise and a reduction amount of snack between meals to achieve the desired body fat percentage may be provided as shown below.

In a case where a woman who is twenty years old with 60 kg of weight enters that she want to reduce 2 kg of fat within two months into the aggregation center "S", the following information will be obtained.

Amount of fat to be reduced a day (Kg)=2 (Kg)/2 (months)=33.3 (g/day)

Since the calorie of 1 Kg of fat is equal to 7200 Kcal, the energy to be consumed a day is:

33.3 (g)×7200 Kcal/1000=240 Kcal

This energy to be consumed can be translated into, for example, a normal speed walking of one and quarter hours per a day, or a light load jogging of three or four minutes per a day, by the calculation based on the table of the consumed energy in the exercise and the age factor used in the Ministry of Health and Welfare.

This energy to be consumed may be translated also into an amount of daily foods to be cut off based on the food constituent table. For example, it may be one piece of donut or one and half glasses of beer with a middle size jug.

Accordingly, the data below is transmitted from the aggregation center "S" to the portable telephone set "T" and is displayed on the display unit 3, and also may be stored in the memory 24.

"One of four menus below shall be employed:

normal speed walking of one and quarter hours a day light load jogging of thirty-four minutes a day a piece of donut reduction a day one and half glass of beer (a middle size jug) reduction a day"

The contents of the above advice is shown only as an example, and various type of advice may be employed including a combination of above menus, an advice of food reduction without disturbing the food balance, an illustration showing a food and a reduced condition in its food (for example, half of an apple is shown in light color).

Though the body fat meter and the portable telephone set are combined in the above embodiment, a blood pressure manometer or a pulse monitor may be combined separately or integrally with the portable telephone set to measure a blood pressure or a pulse rate and to communicate with the aggregation center about the data including the blood pressure and the pulse rate to obtain various advice therefrom based on the specialized analysis, so that this combination is useful to judge own health condition and to manage own health based on the quantity of exercise to be taken and the restriction on the amount of meal.

In case of a blood pressure manometer or a pulse monitor being combined, for example, probe unit such as a cuff attached to the upper arm of a patient and pairs of electrodes attached to a hand or foot or chest of a patient may be connected to the connectors E and F provided on the main body of the portable telephone T and activating unit for activating the probe unit connected to the connectors E and F to cause the probe unit to detect predetermined biological parameters of the patient for calculating a desired health management parameter such as a blood pressure, a pulse rate, etc., may be provided, instead of the constant current generating circuit 22 and the voltage detecting circuit 23.

Though the portable telephone set is employed in the above embodiments as the intelligent terminal unit, other intelligent terminal units such as a portable personal computer with modem or an electronic organizer with communication system may be employed as well.

According to the present invention, as described above, since the body fat meter is mounted on the intelligent terminal unit always carried with, there is little problem of the place for keeping it comparing with the separate type body fat meter, and the body fat percentage can be measured for health management anytime and anywhere. Since the electrodes are provided for each hand and foot, the electric resistance and the body fat percentage can be measured between both hands, between both feet or between hand and foot if necessary, so that the place in the body having the fat may be found. In addition, since the data including the body fat percentage may be stored in the memory for storing the telephone number, the past or various data may be stored and re-displayed at little expense of cost and size. Further, the alarm function enables an accurate and continuous measurement of the body fat, which has to be implemented everyday at the predetermined time, by preventing the measurement from being forgotten or from being implemented at a time other than the predetermined one.

Furthermore, since the body fat meter is mounted on the intelligent terminal unit always carried with and the data may be sent to the aggregation center "S" which has the special information about the health management data analysis and lots of advisory information and also may be received therefrom, an ordinary transmitter can receive various advice based on the specialized analysis by the aggregation center to utilize it in judging own health condition and in managing own health based on the quantity of exercise to be taken, the restriction on the amount of meal or the like.

What is claimed is:

1. A health management system comprising:
   an intelligent terminal unit having a numeral input unit, a display unit, a transmitting and receiving function unit, a memory unit, a body fat meter, and a control unit which calculates a health management indicator based on data input from said numeral input unit and data from said body fat meter and displays a calculated result on said display unit; and
   an aggregation center which performs analysis based on data from said intelligent terminal unit and transmits a result data of said analysis to said intelligent terminal unit;
   wherein data communication is performed between said intelligent terminal unit and said aggregation center;
   the input unit, display unit, transmitting and receiving function unit, memory unit, body fat meter and control unit are integrated into a singe device;
   the health management indicator is a body fat related parameter comprising a body mass index (BMI), and data transmitted from said intelligent terminal unit includes a value of the body fat related parameter calculated by said control unit and stored in said memory unit, wherein the intelligent terminal has at least four electrodes located on the face thereof.

2. A health management system as claimed in claim 1, wherein the body fat meter comprises:
   at least four electrodes located on the face thereof
   at least four electrodes;
   a constant current generating unit which applies a constant current to at least two electrodes among said at least four electrodes; and
   a voltage detecting unit which detects a voltage of at least two electrodes among said at least four electrodes.

3. A health management system as claimed in claim 1, in which data transmitted from said aggregation center includes data indicating an amount of a meal to be reduced.

4. A health management system as claimed in claim 1, in which, by the use of the receiving function of said intelligent terminal unit, various data transmitted from said aggregation center are displayed on said display means.

5. A health management system as claimed in claim 1, in which, by the use of the receiving function of said intelligent terminal unit, various data transmitted from said aggregation center are stored in said memory unit.

6. A health management system as claimed in claim 1, in which said health management indicator is a body fat related parameter, and data transmitted from said aggregation center includes data indicating a desirable range of values of the body fat related parameter.

7. A health management system as claimed in claim 1, in which said health management indicator is a body fat related parameter, and data transmitted from said aggregation center includes data indicating an amount of fat to be reduced.

8. A health management system as claimed in claim 1, in which data transmitted from said aggregation center includes data indicating a quantity of exercise to be taken.

9. A health management system as claimed in claim 1, wherein the intelligent terminal unit comprises a portable telephone.

10. A health management system as claimed in claim 1, wherein the display unit comprises a LCD.

11. A health management system as claimed in claim 1, in which, by the use of the receiving function of said intelligent terminal unit, various data transmitted from said aggregation center are displayed on said display means; and
    said health management indicator is a body fat related parameter, and data transmitted from said aggregation center includes data indicating a desirable range of values of the body fat related parameter.

12. A health management system as claimed in claim 1, in which, by the use of the receiving function of said intelligent terminal unit, various data transmitted from said aggregation center are stored in said memory unit; and
    said health management indicator is a body fat related parameter, and data transmitted from said aggregation center includes data indicating a desirable range of values of the body fat related parameter.

13. A health management system as claimed in claim 1, in which, by the use of the receiving function of said intelligent terminal unit, various data transmitted from said aggregation center are displayed on said display means;
    said health management indicator is a body fat related parameter, and data transmitted from said aggregation center includes data indicating a desirable range of values of the body fat related parameter; and
    said health management indicator is a body fat related parameter, and data transmitted from said aggregation center includes data indicating an amount of fat to be reduced.

14. A health management system as claimed in claim 1, in which, by the use of the receiving function of said intelligent terminal unit, various data transmitted from said aggregation center are stored in said memory unit;
    said health management indicator is a body fat related parameter, and data transmitted from said aggregation center includes data indicating a desirable range of values of the body fat related parameter; and
    said health management indicator is a body fat related parameter, and data transmitted from said aggregation center includes data indicating an amount of fat to be reduced.

15. A health management system as claimed in claim 1, in which data transmitted from said aggregation center includes data indicating a quantity of exercise to be taken; and
    the intelligent terminal unit comprises a portable telephone.

16. A health management system as claimed in claim 1, wherein the intelligent terminal unit comprises a portable telephone; and
    the display unit comprises a LCD.

17. A health management system comprising:
    an intelligent terminal unit having:
    a numeral input unit,
    a display unit,
    a transmitting and receiving function unit,
    a memory unit,
    a probe unit attachable to predetermined portions of the body of a patient to detect predetermined biological parameters of the patient,
    a connector section to which said probe unit is connectable,
    an activating unit which activates said probe unit connected to said connector section to cause said probe unit to detect said predetermined biological parameters of the patient,
    a body fat meter connected to the probe unit and
    a control unit which calculates a desired health management parameter of the patient on the basis of data input from said numeral input unit and the body fat meter for calculating said desired health management parameter of the patient and said predetermined biological parameters detected by said probe unit and displays a calculated result on said display unit; and
    an aggregation center which performs analysis based on a data from said intelligent terminal unit and transmits a result data of said analysis to said intelligent terminal unit is provided;
    wherein data communication is performed between said intelligent terminal unit and said aggregation center;
    the input unit, display unit, transmitting and receiving function unit, memory unit, body fat meter, connector section, activating unit and control unit are integrated into a single device; and
    the desired health management parameter comprises a body fat percentage and a body mass index (BMI).

18. A health management system as claimed in claim 17 in which said health management system is adapted to measure blood pressure.

19. A health management system as claimed in claim 17, in which said health management system is adapted to measure pulse rate.

20. A health management system as claimed in claim 17, wherein the intelligent terminal unit comprises a portable telephone.

21. A health management system as claimed in claim 17 in which said desired health management parameter is a body fat amount.

22. A health management system as claimed in claim 17, wherein the display unit comprises a LCD.

* * * * *

UNITED STATES PATENT AND TRADEMARK OFFICE
CERTIFICATE OF CORRECTION

PATENT NO. : 7,087,016 B2  
APPLICATION NO. : 09/984153  
DATED : August 8, 2006  
INVENTOR(S) : Tamotsu Iwabuchi et al.

It is certified that error appears in the above-identified patent and that said Letters Patent is hereby corrected as shown below:

TITLE PAGE,

Item "(56) References Cited, U.S. PATENT DOCUMENTS", right hand column, change cited reference "6,243,561 B1 * 6/2001 Butler et al. ......600/547" to -- 6,243,651 B1 * 6/2001 Masuo ..........600/547 --.

Signed and Sealed this

Second Day of January, 2007

JON W. DUDAS  
*Director of the United States Patent and Trademark Office*